(12) United States Patent
Yu et al.

(10) Patent No.: US 12,374,433 B1
(45) Date of Patent: Jul. 29, 2025

(54) DECISION SUPPORT SYSTEM USING AN ARTIFICIAL INTELLIGENCE (AI) FRAMEWORK FOR SUGGESTING CODES FOR A CLINICAL RECORD FOR A PATIENT AND RELATED METHODS AND COMPUTER PROGRAM PRODUCTS

(71) Applicant: Change Healthcare Holdings LLC, Nashville, TN (US)

(72) Inventors: Feili Yu, Shoreline, WA (US); Alex Londeree, Austin, TX (US); Lei Qi, Seattle, WA (US); Bo Han, Bothell, WA (US); Wenji Zhang, Redmond, WA (US); Chenda Deng, Fort Collins, CO (US)

(73) Assignee: CHANGE HEALTHCARE HOLDINGS LLC, Nashville, TN (US)

( * ) Notice: Subject to any disclaimer, the term of this patent is extended or adjusted under 35 U.S.C. 154(b) by 188 days.

(21) Appl. No.: 17/656,963

(22) Filed: Mar. 29, 2022

(51) Int. Cl.
  *G16H 10/60* (2018.01)
  *G06N 3/045* (2023.01)
  *G06N 3/08* (2023.01)

(52) U.S. Cl.
  CPC ............ *G16H 10/60* (2018.01); *G06N 3/045* (2023.01); *G06N 3/08* (2013.01)

(58) Field of Classification Search
  CPC ........... G16H 10/60; G06N 3/045; G06N 3/08
  See application file for complete search history.

(56) References Cited

U.S. PATENT DOCUMENTS

| | | | |
|---|---|---|---|
| 10,580,520 B2 | 3/2020 | Schulte et al. | |
| 10,600,504 B2 | 3/2020 | Schneider et al. | |
| 2014/0278553 A1* | 9/2014 | Fritsch | G06Q 30/04 705/2 |
| 2015/0149215 A1* | 5/2015 | Qian | G06F 16/335 705/3 |
| 2017/0323061 A1* | 11/2017 | D'Souza | G16H 40/63 |
| 2021/0358601 A1* | 11/2021 | Pillai | G16H 40/20 |
| 2022/0181032 A1* | 6/2022 | Young | A61B 3/0033 |

* cited by examiner

Primary Examiner — Sheetal R Paulson
(74) Attorney, Agent, or Firm — Myers Bigel, P.A.

(57) ABSTRACT

A method includes receiving a record containing first clinical information associated with a first patient; and automatically processing the record using a multi-stage Artificial Intelligence (AI) engine to generate at least one suggested code for one or more portions of the first clinical information; wherein the multi-stage AI engine comprises: a first module configured to detect whether the first clinical information includes any information associated with a second patient or whether the record contains second clinical information associated with a second patient; a second module configured to partition the first clinical information based on encounter; a third module configured to identify the one or more portions of the first clinical information; or a fourth module configured to identify content highlights within the one or more portions of the first clinical information and associate the content highlights with candidate codes, respectively.

16 Claims, 13 Drawing Sheets

DECISION SUPPORT SYSTEM USING AN ARTIFICIAL INTELLIGENCE (AI) FRAMEWORK FOR SUGGESTING CODES FOR A CLINICAL RECORD FOR A PATIENT AND RELATED METHODS AND COMPUTER PROGRAM PRODUCTS

FIELD

The present inventive concepts relate generally to health care systems and services and, more particularly, to decision support systems for use in coding clinical records.

BACKGROUND

Health care service providers record clinical information associated with patients under their care in clinical charts, which are typically stored as electronic health records. A chart or health record for a patient may be lengthy sometimes exceeding a thousand pages in length. Health care providers typically assign the health records to coders that review the records and assign codes to the various procedures and diagnoses contained therein. The coders may make use of tools or support systems to assist them in assigning codes to the various portions of clinical information contained within the records. The codes are used in generating claims for the services provided by the health care providers for submission to payors for reimbursement. When reviewing claims for payment, payors may also obtain patient medical records and may review the records to identify the evidence within the records and codes associated therewith to support the various services for which the provider is seeking payment. The patient records, however, vary greatly from patient to patient, with some charts containing images, handwriting, tabular data, and/or special symbols. This variety in format can make it difficult to create tools to automate or support the manual process of coding a clinical record.

SUMMARY

According to some embodiments of the inventive concept, a method comprises: receiving a record containing first clinical information associated with a first patient; and automatically processing the record using a multi-stage Artificial Intelligence (AI) engine to generate at least one suggested code for one or more portions of the first clinical information; wherein the multi-stage AI engine comprises: a first module configured to detect whether the first clinical information includes any information associated with a second patient or whether the record contains second clinical information associated with a second patient; a second module configured to partition the first clinical information based on encounter; a third module configured to identify the one or more portions of the first clinical information; or a fourth module configured to identify content highlights within the one or more portions of the first clinical information and associate the content highlights with candidate codes, respectively.

In other embodiments, the multi-stage AI engine includes the fourth module and further comprises: a fifth module configured to remove ones of the content highlights and/or ones of the candidate codes that have been identified and/or associated in error to generate corrected content highlights that are associated with corrected candidate codes, respectively.

In still other embodiments, the multi-stage AI engine further comprises: a sixth module that is configured to generate the at least one suggested code based on the corrected candidate codes that are associated with the corrected content highlights.

In still other embodiments, the sixth module is further configured to present the at least one suggested code to a user.

In still other embodiments, the method further comprises: receiving, using the sixth module, an acceptance or a rejection of the at least one suggested code from the user.

In still other embodiments, the multi-stage AI engine further includes the first module, the second module, and the third module; and the first module, the second module, the third module, the fourth module, and the fifth module are coupled to one another in pipeline fashion.

In still other embodiments, the fourth module comprises a first neural network that is trained using historic patient clinical information records using a first information granularity level and the fifth module comprises a second neural network that is trained using the historic patient clinical information records using a second information granularity level that is coarser than the first information granularity level.

In still other embodiments, the first information granularity is a sentence level granularity and the second information granularity is a section level granularity; and a section comprises multiple sentences.

In still other embodiments, the multi-stage AI engine includes the second module and the third module; and the one or more portions of the clinical information are in one or more partition sections, respectively, of the first clinical information, each of the one or more partition sections corresponding to a single encounter.

In still other embodiments, the method further comprises: using the third module to identify the one or more portions of the first clinical information by disregarding irrelevant encounters.

In still other embodiments, the irrelevant encounters comprise irrelevant clinical information directed to previous medications prescribed to the first patient, family and social history, allergies, lab results, radiology results, and/or previous diagnoses assigned to the first patient.

In still other embodiments, the method further comprises: converting the record into a text record using optical character recognition (OCR) responsive to receiving the record; wherein automatically processing the record using the multi-stage AI engine comprises automatically processing the text record using the multi-stage AI engine.

In still other embodiments, the at least one suggested code is an International Classification of Diseases (ICD) code or a Current Procedural Terminology (CPT) code.

In some embodiments of the inventive concept a system comprises a processor; and a memory coupled to the processor and comprising computer readable program code embodied in the memory that is executable by the processor to perform operations comprising: receiving a record containing first clinical information associated with a first patient; and automatically processing the record using a multi-stage Artificial Intelligence (AI) engine to generate at least one suggested code for one or more portions of the first clinical information; wherein the multi-stage AI engine comprises: a first module configured to detect whether the clinical information includes any information associated with a second patient or whether the record contains second clinical information associated with a second patient; a second module configured to partition the first clinical information based on encounter; a third module configured to identify the one or more portions of the first clinical information; or a fourth module configured to identify content highlights within the one or more portions of the first clinical information and associate the content highlights with candidate codes, respectively.

In further embodiments, the multi-stage AI engine includes the second module and the third module; and the one or more portions of the clinical information are in one or more partition sections, respectively, of the first clinical information, each of the one or more partition sections corresponding to a single encounter.

In still further embodiments, the operations further comprise: using the third module to identify the one or more portions of the first clinical information by disregarding irrelevant encounters.

In still further embodiments, the irrelevant encounters comprise irrelevant clinical information directed to previous medications prescribed to the first patient, family and social history, allergies, lab results, radiology results, and/or previous diagnoses assigned to the first patient.

In some embodiments of the inventive concept, a computer program product, comprises a non-transitory computer readable storage medium comprising computer readable program code embodied in the medium that is executable by a processor to perform operations comprising: receiving a record containing first clinical information associated with a first patient; and automatically processing the record using a multi-stage Artificial Intelligence (AI) engine to generate at least one suggested code for one or more portions of the first clinical information; wherein the multi-stage AI engine comprises: a first module configured to detect whether the clinical information includes any information associated with a second patient or whether the record contains second clinical information associated with a second patient; a second module configured to partition the first clinical information based on encounter; a third module configured to identify the one or more portions of the first clinical information; or a fourth module configured to identify content highlights within the one or more portions of the first clinical information and associate the content highlights with candidate codes, respectively.

In other embodiments, the multi-stage AI engine includes the second module and the third module; and the one or more portions of the clinical information are in one or more partition sections, respectively, of the first clinical information, each of the one or more partition sections corresponding to a single encounter.

In still other embodiments, the operations further comprise: using the third module to identify the one or more portions of the first clinical information by disregarding irrelevant encounters; and wherein the irrelevant encounters comprise irrelevant clinical information directed to previous medications prescribed to the first patient, family and social history, allergies, lab results, radiology results, and/or previous diagnoses assigned to the first patient.

Other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
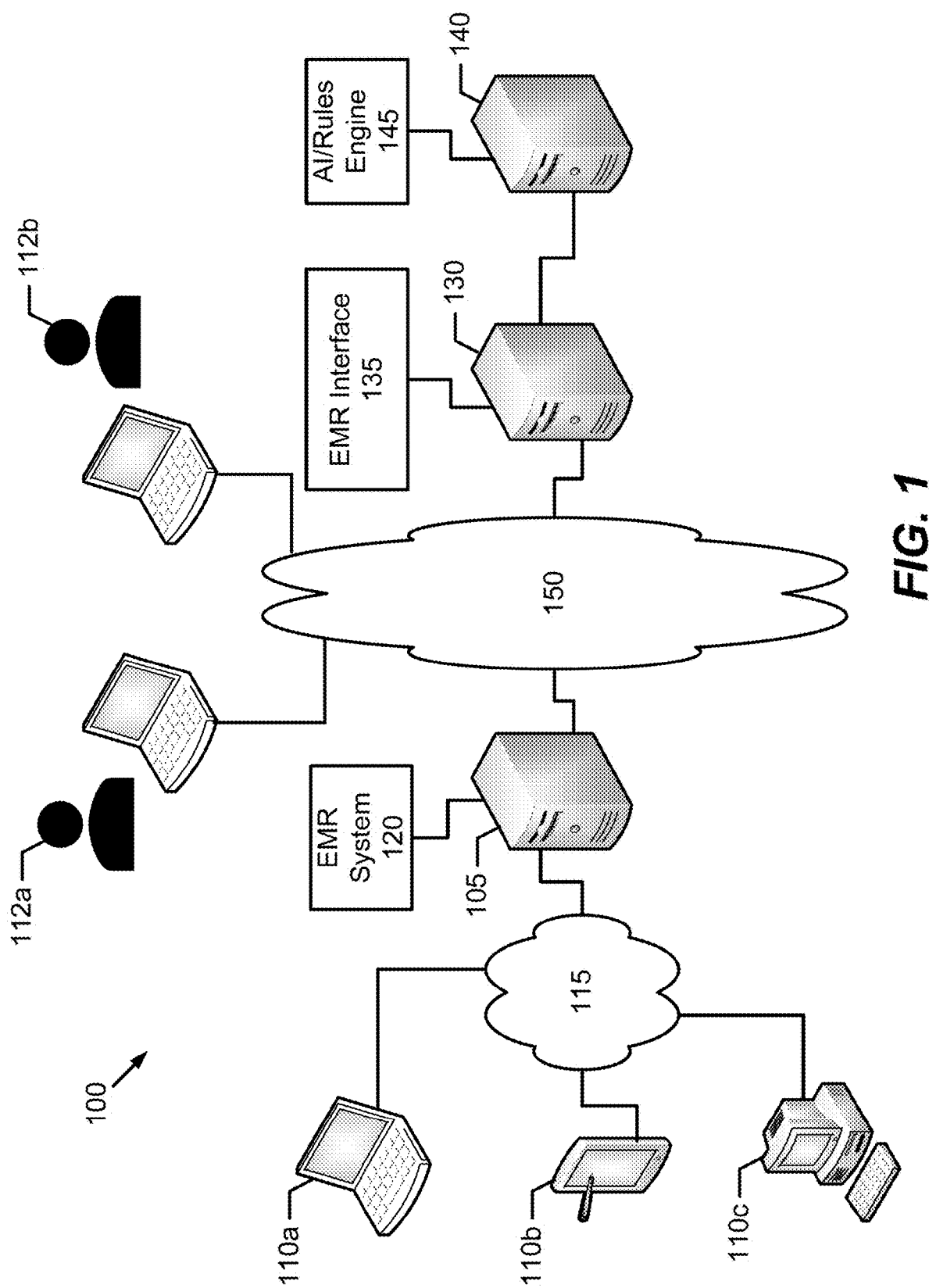
FIG. 1 is a block diagram that illustrates a communication network including an intelligent coding Decision Support System (DSS) in accordance with some embodiments of the inventive concept.

In the following detailed description, numerous specific details are set forth to provide a thorough understanding of embodiments of the inventive concept. However, it will be understood by those skilled in the art that embodiments of the inventive concept may be practiced without these specific details. In some instances, well-known methods, procedures, components, and circuits have not been described in detail so as not to obscure the inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "provider" may mean any person or entity involved in providing health care products and/or services to a patient.

Embodiments of the inventive concept are described herein in the context of a Decision Support System (DSS) that includes one or more Artificial Intelligence (AI) engines for processing patient records, which include clinical information, and suggesting codes therefor. The embodiments of the DSS are described with respect to the use of one or more multi-layer neural networks and logical rules. It will be understood, however, that embodiments of the inventive concept are not limited to neural network implementations of the DSS and that other types of AI systems may be used including, but not limited to, a machine learning system, a deep learning system, a natural language processing system, and/or computer vision system. Moreover, it will be understood that the multi-layer neural network is a multi-layer artificial neural network comprising artificial neurons or nodes and does not include a biological neural network comprising real biological neurons. The neural networks and AI engines described herein may be configured to transform a memory of a computer system to include one or more data structures, such as, but not limited to, arrays, extensible arrays, linked lists, binary trees, balanced trees, heaps, stacks, and/or queues. These data structures can be configured or modified through the AI training process to improve the efficiency of a computer system when the computer system operates in an inference mode to make an inference, prediction, classification, suggestion, or the like in response to input information or data provided thereto.

Embodiments of the inventive concept are described herein with respect to use of a DSS for processing clinical patient records and suggesting codes therefor. These codes may include, but are not limited to, International Classification of Diseases (ICD) codes and/or Current Procedural Terminology (CPT) codes. It will be understood that embodiments of the inventive concept are not limited to use of a DSS for processing clinical patient records and suggesting codes therefor, but can be applied to classification problems in general.

A typical workflow for coding clinical medical records associated with patients involves a mixture of automation, third-party tools, and manual effort. For example, in the example of a payor reviewing medical records to search for evidence and/or codes from the record that would support one or more line items on a claim, the process may begin by filtering medical records using an internal tool to identify the more high value records. Human agents may then split the records manually into multiple files with each file representing an encounter with a provider. A third-party tool may then be used in suggesting codes with the agents approving or rejecting the codes based on evidence highlighted by the tool in the record. This workflow, however, may suffer from various drawbacks including, for example, low productivity due to the mixture of manual and automated processes, which may be more complex as both internal and third-party tools may be used. The workflow may have relatively high costs associated therewith due to the intensive human agent review that is involved and the use of third-party vendors to supply tools. Compliance with Personal Health Information (PHI) regulations may further increase the cost. The workflow may also be subject to market risk due the dependency on vendors for tools. If a vendor does not continue to support a tool after a contract expires, for example, the entire workflow may be impacted.

Some embodiments of the inventive concept stem from a recognition of the above-described costs and risks in extracting codes from a medical record in which a combination of human effort, internal support tools, and third-party support tools are used. Some embodiments of the inventive concept may provide an intelligent coding DSS that is based on a muti-stage AI engine or framework in which multiple AI modules are coupled to one another in pipeline fashion to process a patient record containing clinical information and generate one or more suggested codes for one or more portions of the clinical information. The multi-stage AI engine may automate all the operations to generate suggested codes based on a patient's clinical record before presenting the codes to a human agent for an acceptance or rejection decision. According to some embodiments, the multi-stage AI engine may include one or more of the following modules: an Optical Character Recognition (OCR) module configured to convert the patient record into a text record; a PHI violation detection module configured to detect whether a record includes any mixture of information associated with different patients; an encounter detection module configured to partition the clinical information in the patient record based on encounter; a section evaluation module configured to identify, for each encounter, one or more portions of the clinical information in the record for which one or more codes may be suggested therefor; an entity recognition and code mapping module configured to identify content highlights within the one or more portions of the clinical information and to associate those content highlights with candidate codes; and a code mapping audit module that is configured to remove ones of the content highlights and/or ones of the candidate codes that have been identified and/or associated in error to generate corrected content highlights that are associated with corrected candidate codes, respectively. The code mapping audit module may be further configured to generated one or more suggested codes based on the corrected candidate codes that are associated with the corrected content highlights and may present these one or more suggested codes to a user for acceptance or rejection.

The multi-stage AI engine or framework may automate the operations involved in associating codes with portions of a medical record containing clinical information for a patient without the need for additional internal tools, third-party tools, or processing by human coders. The AI engine or framework may automatically process the clinical record and suggest one or more codes for portions of the clinical information contained therein. A human coder need only be involved in the coding process at the stage of reviewing suggested codes for a patient's clinical record, which are output from the multi-stage AI engine.

Referring to FIG. 1, a communication network 100 including an intelligent coding DSS, in accordance with some embodiments of the inventive concept, comprises a health care facility server 105 that is coupled to devices 110a, 110b, and 110c via a network 115. The health care facility may be any type of health care or medical facility, such as a hospital, doctor's office, specialty center (e.g., surgical center, orthopedic center, laboratory center etc.), or the like. The health care facility server 105 may be configured with an Electronic Medical Record (EMR) system module 120 to manage patient files and facilitate the entry of orders for patients via health care service providers ("providers"). Although shown as one combined system in FIG. 1, it will be understood that some health care facilities use separate systems for electronic medical record management and order entry management. The providers may use devices, such as devices 110a, 110b, and 110c to manage patients' electronic charts or records and to issue orders for the patients through the EMR system 120. An order may include, but is not limited to, a treatment, a procedure (e.g., surgical procedure, physical therapy procedure, radiologic/imaging procedure, etc.) a test, a prescription, and the like. The network 115 communicatively couples the devices 110a, 110b, and 110c to the health care facility server 105. The network 115 may comprise one or more local or wireless networks to communicate with the health care facility server 105 when the health care facility server 105 is located in or proximate to the health care facility. When the health care facility server 105 is in a remote location from the health care facility, such as part of a cloud computing system or at a central computing center, then the network 115 may include one or more wide area or global networks, such as the Internet.

According to some embodiments of the inventive concept, an intelligent coding DSS may be provided to assist entities, such as providers, payors, auditors, data entry personnel, and others, which are represented as users 112a and 112b in FIG. 1, in coding patient records, extracting evidence for codes from patient records, auditing existing codes and clinical information corresponding thereto, and the like. The intelligent coding DSS may include a health care facility interface server 130, which includes an EMR interface system module 135 to facilitate the transfer of information between the EMR system 120, which the providers use to manage patient charts and records and issue orders, and a coding suggestion server 140, which includes an AI/Rules engine module 145. The coding suggestion server 140 and AI/Rules engine module 145 may be configured to receive patient records from the EMR system 120 by way of the health care facility interface server 130 and EMR interface module 135. The coding suggestion server 140 and AI/Rules engine 145 may process each page of each patient clinical record using a multi-stage AI engine as will be described below with respect to FIG. 2 to generate coding suggestions for one or more portions of the clinical information contained therein.

It will be understood that the division of functionality described herein between the coding suggestion server 140/AI/Rules engine module 145 and the health care facility interface server 130/EMR interface module 135 is an example. Various functionality and capabilities can be moved between the coding suggestion server 140/AI/Rules engine module 145 and the health care facility interface server 130/EMR interface module 135 in accordance with different embodiments of the inventive concept. Moreover, in some embodiments, the coding suggestion server 140/AI engine module 145 and the health care facility interface server 130/EMR interface module 135 may be merged as a single logical and/or physical entity.

A network 150 couples the health care facility server 105, the health care facility interface server 130, and the users 112a, 112b together. The network 150 may be a global network, such as the Internet or other publicly accessible network. Various elements of the network 150 may be interconnected by a wide area network, a local area network, an Intranet, and/or other private network, which may not be accessible by the general public. Thus, the communication network 150 may represent a combination of public and private networks or a virtual private network (VPN). The network 150 may be a wireless network, a wireline network, or may be a combination of both wireless and wireline networks.

The coding suggestion service provided through the health care facility interface server 130, EMR interface module 135, coding suggestion server 140 and AI/Rules engine module 145 to automatically suggest codes for one or more portions of clinical information in a patient clinical record may, in some embodiments, be embodied as a cloud service. For example, entities may integrate their clinical record processing system with the code suggestion service and access the service as a Web service. In some embodiments, the code suggestion service may be implemented as a Representational State Transfer Web Service (RESTful Web service).

Although FIG. 1 illustrates an example communication network including an intelligent coding DSS for suggesting codes for one or more portions of a patient clinical record, it will be understood that embodiments of the inventive subject matter are not limited to such configurations, but are intended to encompass any configuration capable of carrying out the operations described herein.

Figure 2:
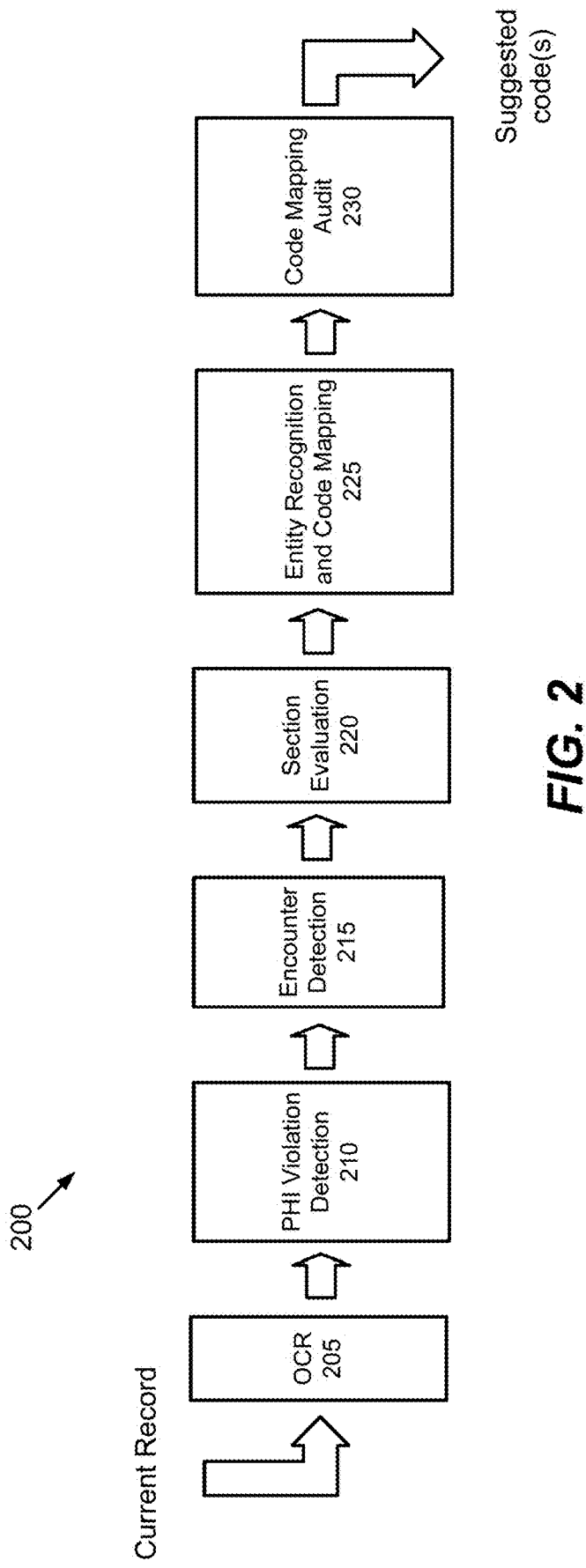
FIG. 2 is a block diagram illustrating a multi-stage Artificial Intelligence (AI) engine used in the intelligent DSS of FIG. 1 in accordance with some embodiments of the inventive concept.

FIG. 2 is a block diagram illustrating a multi-stage AI engine 200 used in the intelligent DSS of FIG. 1 in accordance with some embodiments of the inventive concept. As shown in FIG. 2, the multi-stage AI engine 200 includes a plurality of modules coupled in pipeline fashion. The multi-stage AI engine may automate the operations to generate suggested codes based on a patient's clinical record and then present the suggested codes to a user for acceptance or rejection. The multi-stage AI engine 200 includes the following serially connected modules: an Optical Character Recognition (OCR) module 205 configured to convert the patient record into a text record; a PHI violation detection module configured to detect whether a record includes any mixture of information associated with different patients 210; an encounter detection module 215 configured to partition the clinical information in the patient record based on encounter; a section evaluation module 220 configured to identify, for each encounter, one or more portions of the clinical information in the record for which one or more codes may be suggested therefor; an entity recognition and code mapping module 225 configured to identify content highlights within the one or more portions of the clinical information and to associate those content highlights with candidate codes; and a code mapping audit module 230 that is configured to remove ones of the content highlights and/or ones of the candidate codes that have been identified and/or associated in error to generate corrected content highlights that are associated with corrected candidate codes, respectively. The code mapping audit module 230 may be further configured to generate one or more suggested codes based on the corrected candidate codes that are associated with the corrected content highlights and may present these one or more suggested codes to a user for acceptance or rejection. In other embodiments, a separate module may be included to facilitate communication of suggested codes to a user and to receive input with respect to acceptance or rejection therefrom.

Some of the modules in the multi-stage AI engine 200 may be embodied as an artificial multi-layer neural network. For example, the PHI violation detection module 210, the encounter detection module 215, the entity recognition and code mapping module 225, and the code mapping audit module 230 may each be embodied as a separate multi-layer neural network Referring now to FIG. 3, artificial neural networks are generally based on the same fundamental concepts. The data to be analyzed is broken into elements that can be distributed across an array of nodes, e.g., pixels for an image-recognition task or parameters for a forecasting problem. The artificial neural network 300 may consist of two or more layers of nodes, which can be connected to each other in a variety of different ways.

Figure 3:
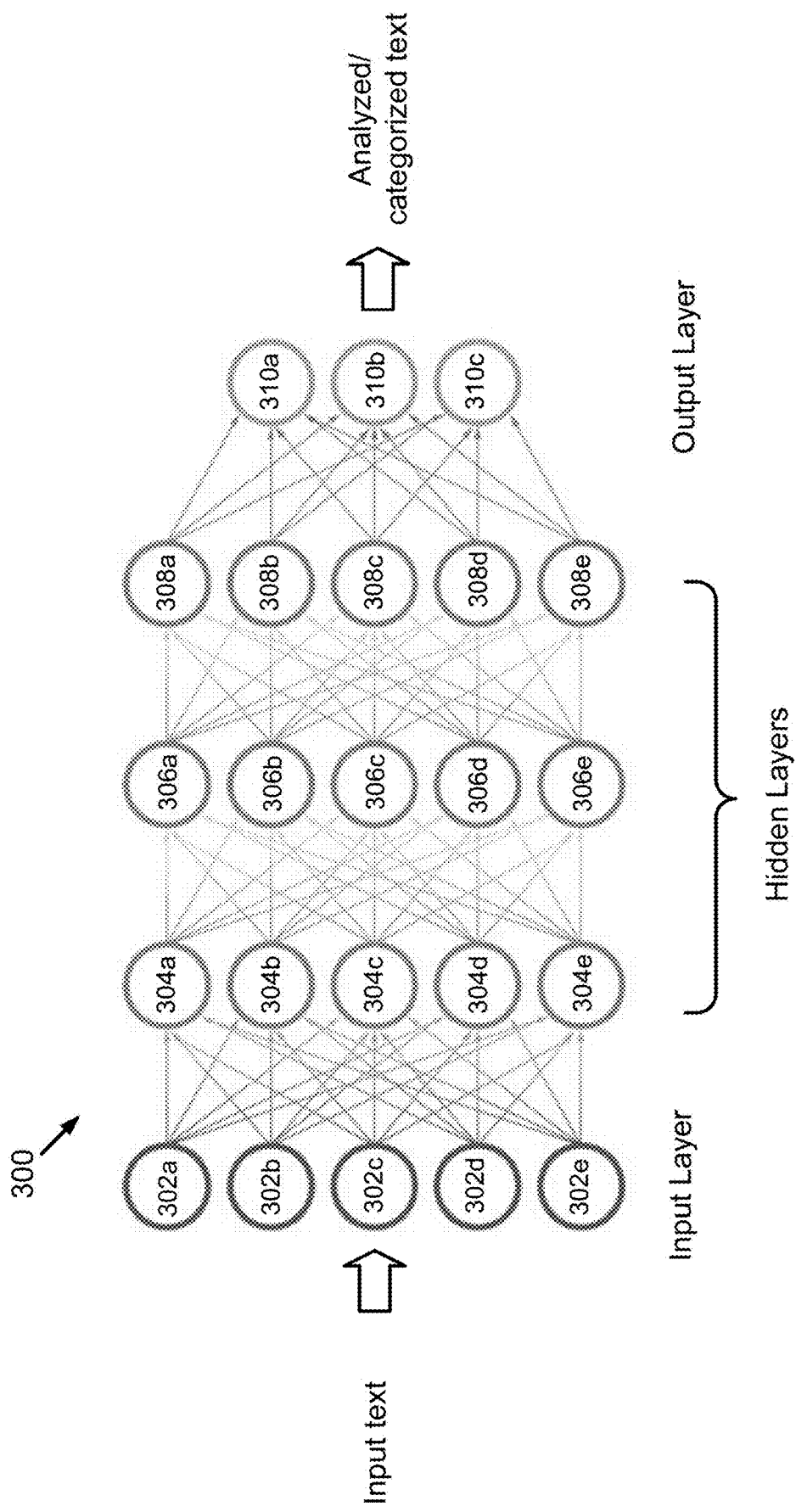
FIG. 3 is a diagram of an artificial neural network that can be used in the multi-stage AI engine of FIG. 2 in accordance with some embodiments of the inventive concept.

In a fully connected layer, every node in layer A connects to every node in layer B. In a convolutional layer, in contrast, a filter is defined that assigns a small portion of layer A to each node in layer B. In the example where layers A and B are fully or densely connected, each node in layer A sends its data element to each node in layer B. In the example of FIG. 3, each of the layers is fully or densely connected, but this is merely an example. In other embodiments, only a portion of the artificial neural network 300 layers may be fully or densely connected. Each node in layer B multiplies each of the data elements received from the layer A nodes by a respective weight that corresponds to the layer A node from which the data element was received and then sums these products for all of the nodes in layer A. Each node in layer B may then apply an activation function to the summation and forward the output on to the nodes in the next layer. The process repeats for as many layers as there are in the artificial neural network 300.

In the example of FIG. 3, the artificial neural network 300 includes a plurality of node layers comprising an input layer, one or more hidden layers, and an output layer. In the example shown in FIG. 3, an input layer comprises five nodes or neurons 302a, 302b, 302c, 302d, and 302e and an output layer comprises three nodes or neurons 310a, 310b, and 310c. In the example shown, three hidden layers connect the input layer to the output layer including a first hidden layer comprising five nodes or neurons 304a, 304b, 304c, 304d, and 304e, a second hidden layer comprising five nodes or neurons 306a, 306b, 306c, 306d, and 306e, and a third hidden layer comprising five nodes or neurons 308a, 308b, 308c, 308d, and 308e. Other embodiments may use more or fewer hidden layers. Each node or neuron connects to another and has an associated weight and threshold. If the output of any individual node or neuron is above the specified threshold value, that node is activated, sending data to the next layer of the network. Otherwise, no data is passed along to the next layer of the network.

Each individual node or neuron may be viewed as implementing a linear regression model, which is composed of input data, weights, a bias (or threshold), and an output. Once an input layer is determined, weights are assigned. These weights help determine the importance of any given variable, with larger ones contributing more significantly to the output compared to other inputs. All inputs are then multiplied by their respective weights and then summed, i.e., a MAC operation. In FIG. 3, node or neuron 306a, for example, receives inputs corresponding to the outputs of nodes or neurons 304a, 304b, 304c, 304d, and 304e. These inputs are multiplied by their corresponding weights and summed at node or neuron 306a. Afterward, the output is passed through an activation function (e.g., a Rectified Linear Unit (ReLU) activation function), which determines the output. If that output exceeds a given threshold, it activates the node by passing data to the next layer in the network. This results in the output of one node becoming in the input of the next node. This process of passing data from one layer to the next layer is an example of a feedforward artificial neural network.

The artificial neural network 300 relies on training data to learn and improve its accuracy over time. Once the various parameters of the artificial neural network 300 are tuned and refined for accuracy, it can be used, among other applications, to analyze/categorize text at the output layer 310. The output of the AI neural network may be analyzed/categorized text that may be used for a variety of purposes including identifying portions of relevant text from a larger document, such as a patient's clinical health care record, searching for portions of text that include information on a topic and/or answers to one or more questions, or the like.

Figure 4:
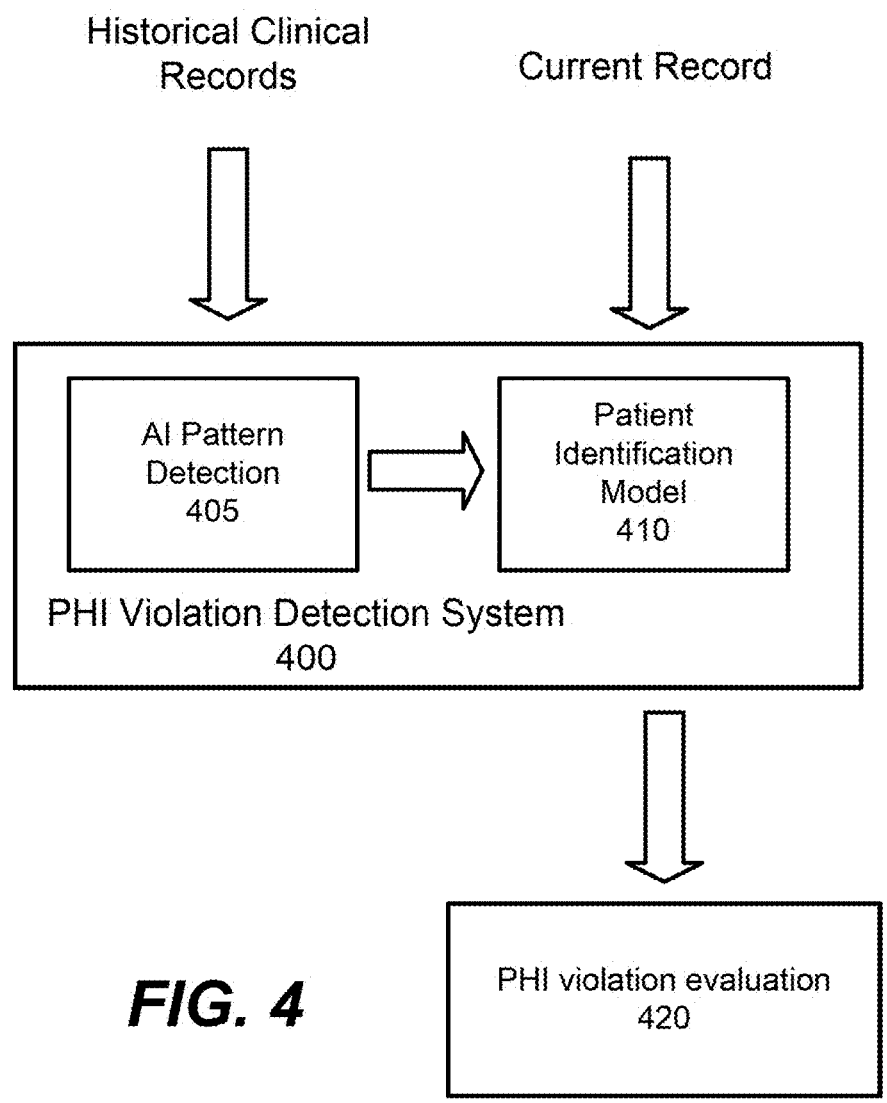
FIG. 4 is a block diagram that illustrates a PHI violation detection system in accordance with some embodiments of the inventive concept.

FIG. 4 is a block diagram that illustrates embodiments of the PHI violation detection module 210 in which an AI engine is used to process the record to detect whether a record includes any mixture of information associated with different patients. Various patient identification parameters may appear in various locations in patient records and may not always explicitly identify the parameter as such. For example, the "patient name" parameter may appear in a record with the patient's actual name listed, but without the parameter label "patient name" adjacent thereto. As shown in FIG. 4, the PHI violation detection system 400 includes an AI engine, which may be a machine learning engine or neural network comprising an AI pattern detection module 405 and a patient identification parameter extraction model 410. The AI pattern detection module 405 is configured to receive historical clinical records for historical patients, and may learn associations between patient identification parameters and the manners in which the historical clinical information is organized in the records. These associations may, for example, facilitate the ability to identify the presence of a value for a patient identification parameter in circumstances in which the label for the patient identification parameter is missing (e.g., a patient's name is present without the associated label "patient name."). The AI pattern detection module 405 may then generate a patient identification parameter extraction model 410 based on these learned associations, which can be used to process a current record. The patient identification parameter extraction model 410 may output instances in the record in which multiple patients are identified. For example, the record may be presumed to correspond to a first patient, but some clinical information contained therein corresponds to a second patient. As another example, the record may be presumed to correspond to a first patient, but the record data or metadata appears to indicate the record corresponds to a second patient. Example embodiments of a PHI violation detection system are described, for example, in U.S. patent application Ser. No. 17/449,334, filed Sep. 29, 2021, entitled "METHODS, SYSTEMS, AND COMPUTER PROGRAM PRODUCTS FOR AUTOMATICALLY PROCESSING A CLINICAL RECORD FOR A PATIENT TO DETECT PROTECTED HEALTH INFORMATION (PHI) VIOLATIONS," the disclosure of which is incorporated herein by reference.

Figure 5:
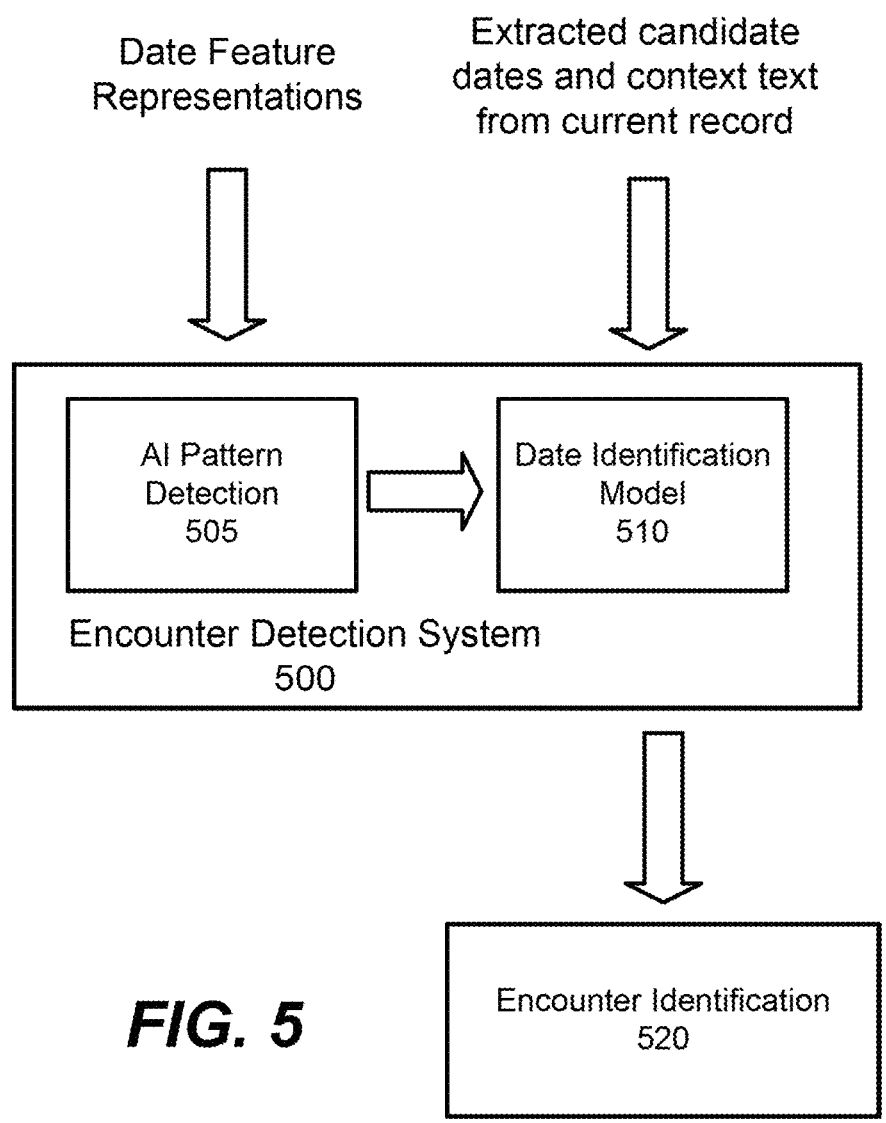
FIG. 5 is a block diagram that illustrates an encounter detection system in accordance with some embodiments of the inventive concept.

FIG. 5 is a block diagram that illustrates embodiments of the encounter detection module 215 in which an AI engine is used to process the record to partition the clinical information based on encounter. A medical chart typically includes many different types of dates, such as date of birth, date to take a medicine, etc. and these dates may be written in a variety of different types of formats. e.g., "01/01/2025," "2025/01/01," "01-01-2025," "Jan. 1, 2025," "2025 Jan. 1," etc. As shown in FIG. 5, the encounter detection system 500 includes an AI engine, which may be a machine learning engine or neural network comprising an AI pattern detection module 505 and a date identification model 510. The AI pattern detection module 505 is configured to receive different date feature representations based on a plurality of different types of embeddings and may learn the different types of representations used to indicate dates along with the various contexts in which dates are used. The AI pattern detection module 505 may then generate a date identification model 510 based on these learned associations, which can be used to process extracted candidate dates and context text from a current record. The date identification model 510 may identify the locations in the patient record corresponding to the various instances in which a patient had an encounter with a provider 520. The clinical information in the patient record may, therefore, be partitioned based on encounter dates.

Figure 6:
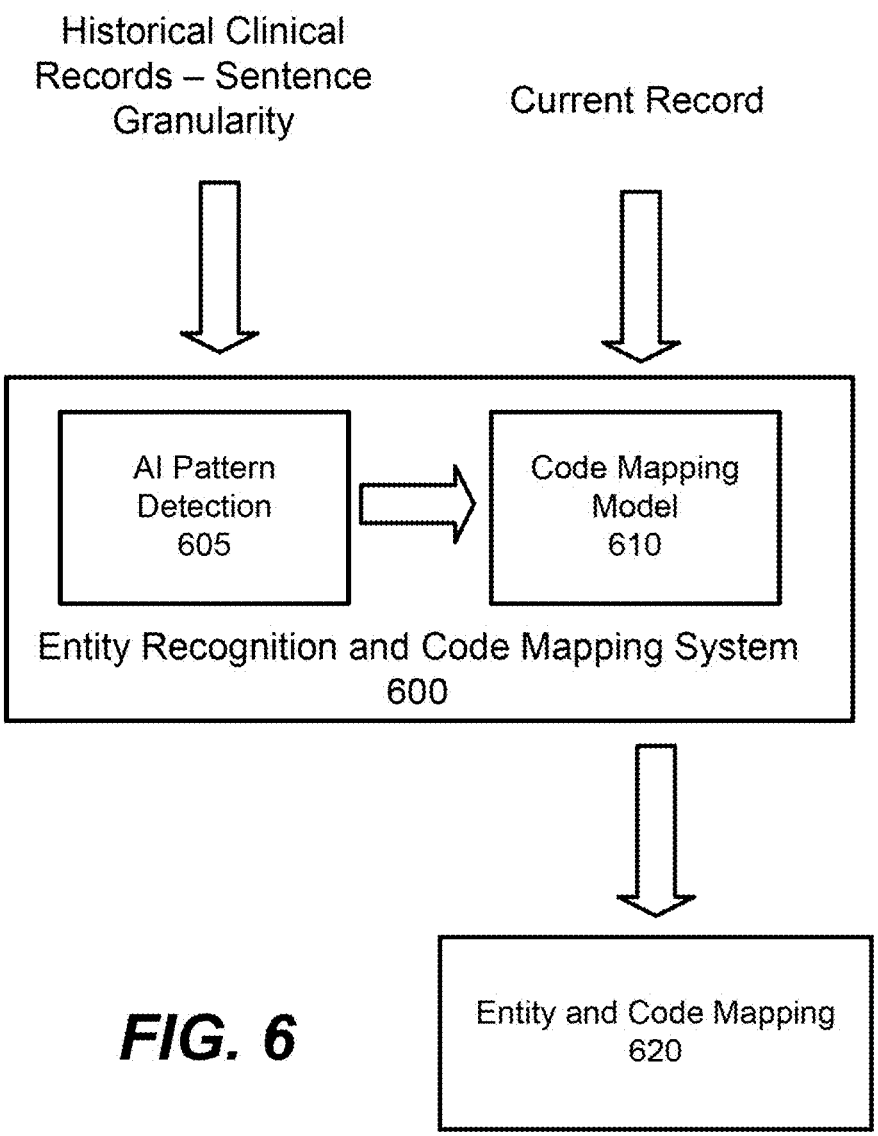
FIG. 6 is a block diagram that illustrates an entity recognition and code mapping system in accordance with some embodiments of the inventive concept.

FIG. 6 is a block diagram that illustrates embodiments of the entity recognition and code mapping module 225 in which an AI engine is used to process the record to identify content highlights within one or more portions of the clinical information in a patient record and associate these content highlights with candidate codes for each encounter. As shown in FIG. 6, the entity recognition and code mapping system 600 includes an AI engine, which may be a machine learning engine or neural network comprising an AI pattern detection module 605 and a code mapping model 610. The AI pattern detection module 605 is configured to receive sentences from historic patient clinical information records for learning associations between these sentences and candidate codes. By using sentence level granularity, improved code coverage across the library of possible codes may be obtained. The AI pattern detection module 605 may then generate a code mapping model 610 based on these learned associations, which can be used to process a current record to identify content highlights from the clinical information that are associated with one or more codes 620. A negation operation may be performed to disregard entities from the clinical information that are non-supportive of a code, e.g., statements that a patient doesn't have a particular disease, or codes that are redundant, e.g., the patient has diabetes, but other text indicates that the patient has diabetes with peripheral neuropathy obviating the need to code the diabetes diagnosis. In this case, the more detailed diagnosis diabetes with peripheral neuropathy is preferred over the more general diagnosis of diabetes.

Figure 7:
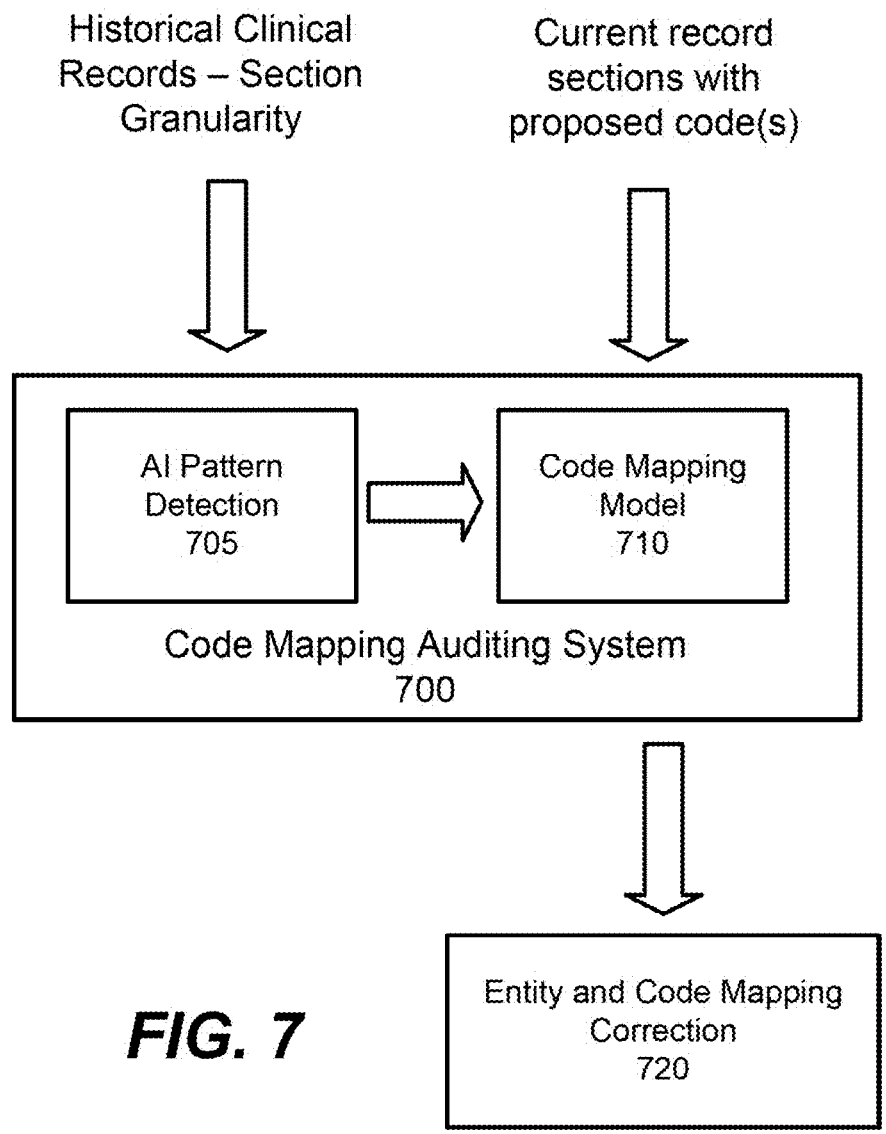
FIG. 7 is a block diagram that illustrates a code mapping auditing system in accordance with some embodiments of the inventive concept.

FIG. 7 is a block diagram that illustrates embodiments of the code mapping audit module 230 in which an AI engine is used to evaluate the associations between the content highlights and candidate codes output from the entity recognition and code mapping module 225. As shown in FIG. 7, the encounter detection system 700 includes an AI engine, which may be a machine learning engine or neural network comprising an AI pattern detection module 705 and a code mapping model 710. The AI pattern detection module 705 is configured to receive sections of sentences from historic patient clinical information records for learning associations between these sentences and candidate codes. By using section level granularity, i.e., multiple sentences, additional context and semantic relationship information may be incorporated into the training process. The AI pattern detection module 705 may then generate a code mapping model 710 based on these learned associations, which can be used to process a current record, which includes content highlights associated with candidate codes based on the output of the entity recognition and code mapping module 225, to identify those content highlights and/or candidate codes that have been identified and/or associated with one another in error 720.

Figure 8:
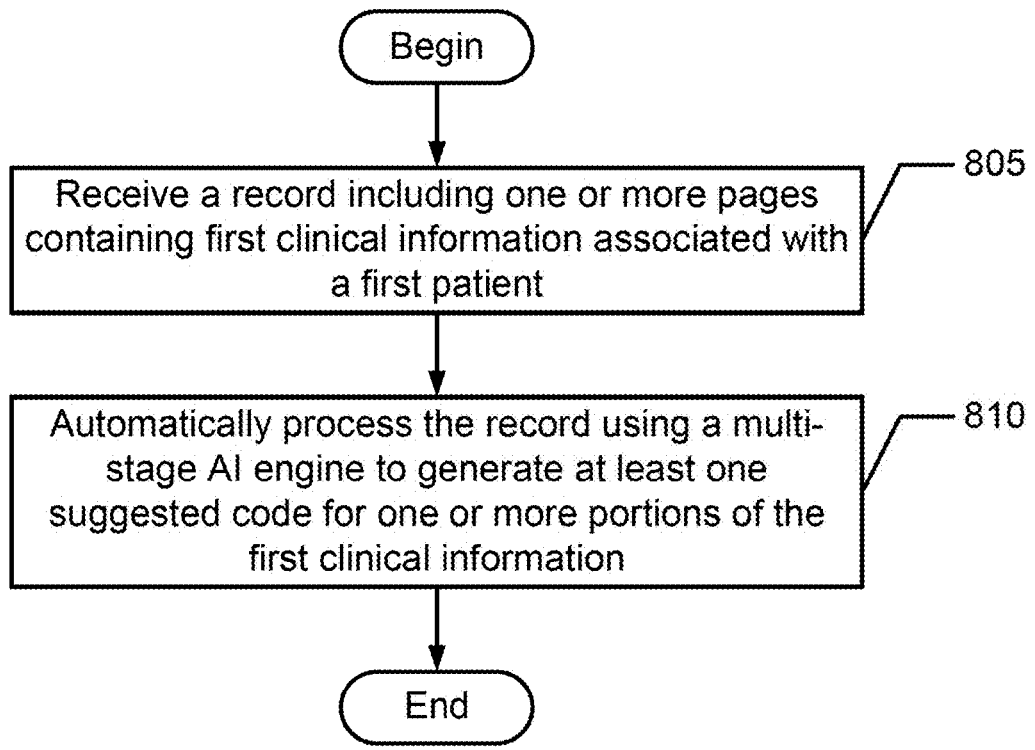
FIGS. 8-14 are flowcharts that illustrate operations of the intelligent coding DSS in accordance with some embodiments of the inventive concept.
Figure 9:
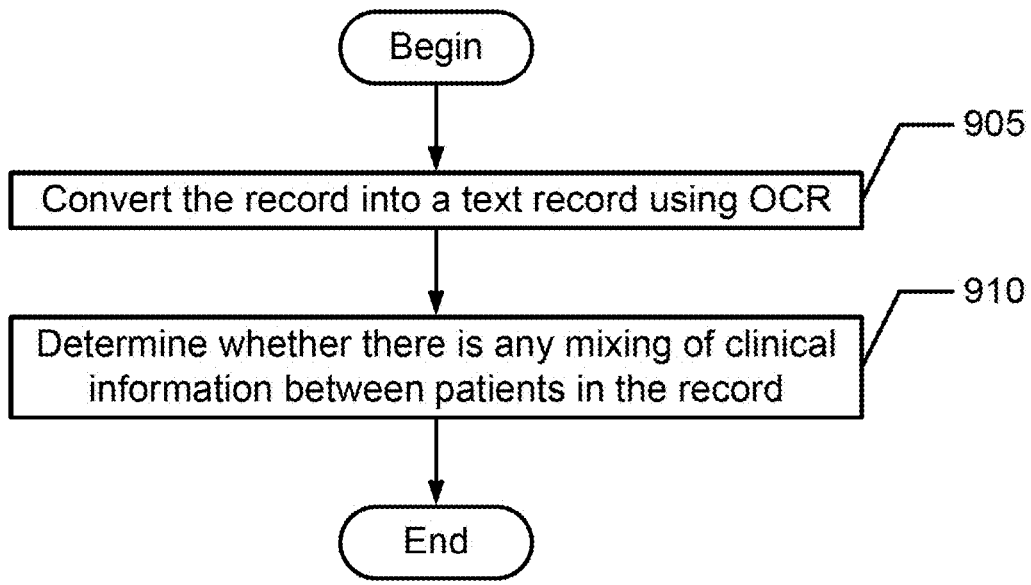

FIGS. 8-14 are flowcharts that illustrate operations of the intelligent coding DSS in accordance with some embodiments of the inventive concept. Referring now to FIG. 8 and FIG. 2, operations begin at block 805 where the OCR module 205 receives a patient record including one or more pages containing clinical information associated with the patient. The intelligent DSS coding system 200 may then automatically process the record using a multi-stage AI engine to generate one or more suggested codes for one or more portions of the clinical information. Referring to FIG. 9, to facilitate processing the patient record, the OCR module 205 may convert the record into a text record using OCR at block 905. The PHI violation detection module 210 may then determine whether there is any mixing of clinical information between patients in the record at block 910. In some embodiments, the PHI violation evaluation may involve determining whether the record is properly associated with a first patient, but includes clinical information on one or more pages associated with a second patient and/or whether the record is identified as corresponding to a first patient, but in fact corresponds to a second patient.

Figure 10:
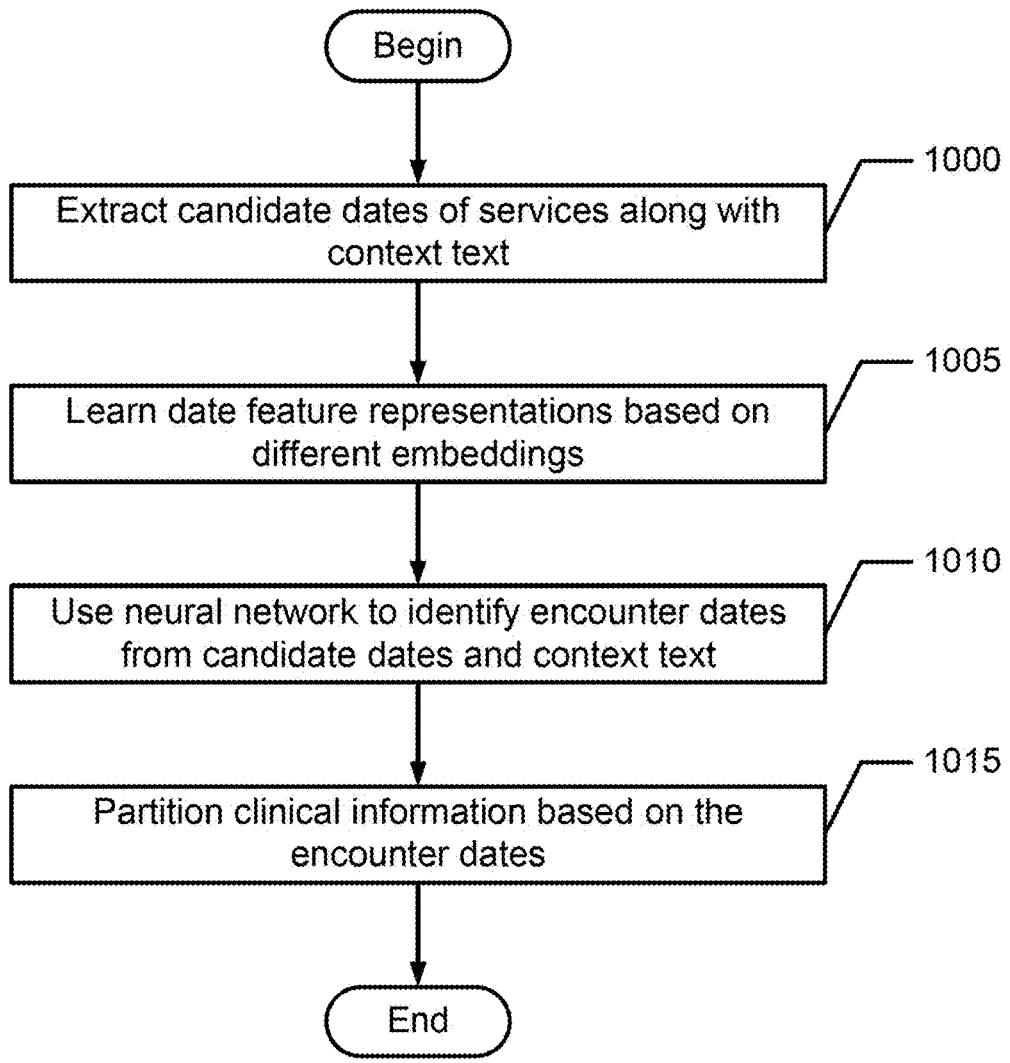

Once the record has been evaluated for PHI violations, the record may be partitioned based on encounter. Referring to FIG. 10, operations begin at block 1000 where candidate dates of services are extracted from the record along with context text that border or surround the candidate dates. An AI engine used in the encounter detection module 215, such as the AI engine described above with respect to FIG. 5, receives different date feature representations based on a plurality of different types of embeddings and may learn the different types of representations used to indicate dates along with the various contexts in which dates are used at block 1005. Based on this training, a neural network, for example, may be used to identify encounter dates from the candidate dates and context text obtained from the patient record at block 1010 using, for example, named entity recognition. In some embodiments, the encounter dates may be further filtered by converting each encounter date into a standard format. Those encounter dates that cannot be converted successfully may be discarded. The encounter detection module 215 may partition the clinical information based on the encounter dates at block 1015.

Figure 11:
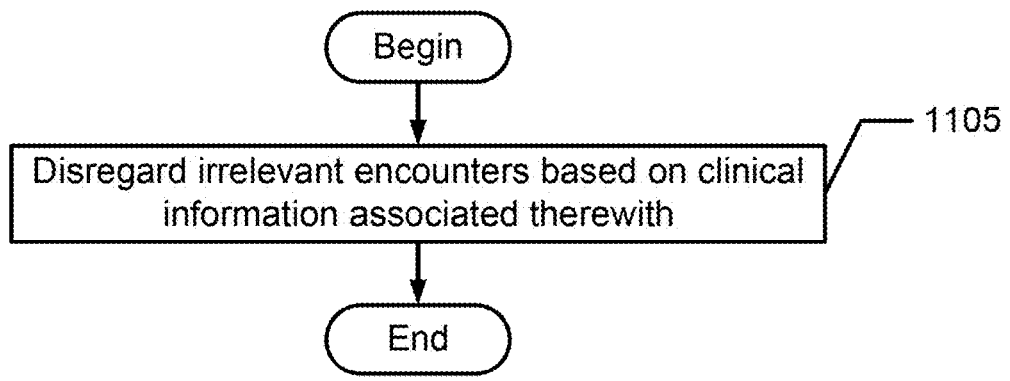

Not all encounters, however, may be useful for identifying content highlights that may be coded. Referring to FIG. 11, according to some embodiments of the inventive concept, the section evaluation module 220 may be configured to disregard irrelevant encounters based on the clinical information contained therein at block 1105. The section evaluation module 220 may, in some embodiments, use a rules-based system to identify irrelevant encounters, such as encounters that include only clinical information directed to previous medications, family and social history, allergies, lab results, radiology results, and/or previous diagnoses.

Figure 12:
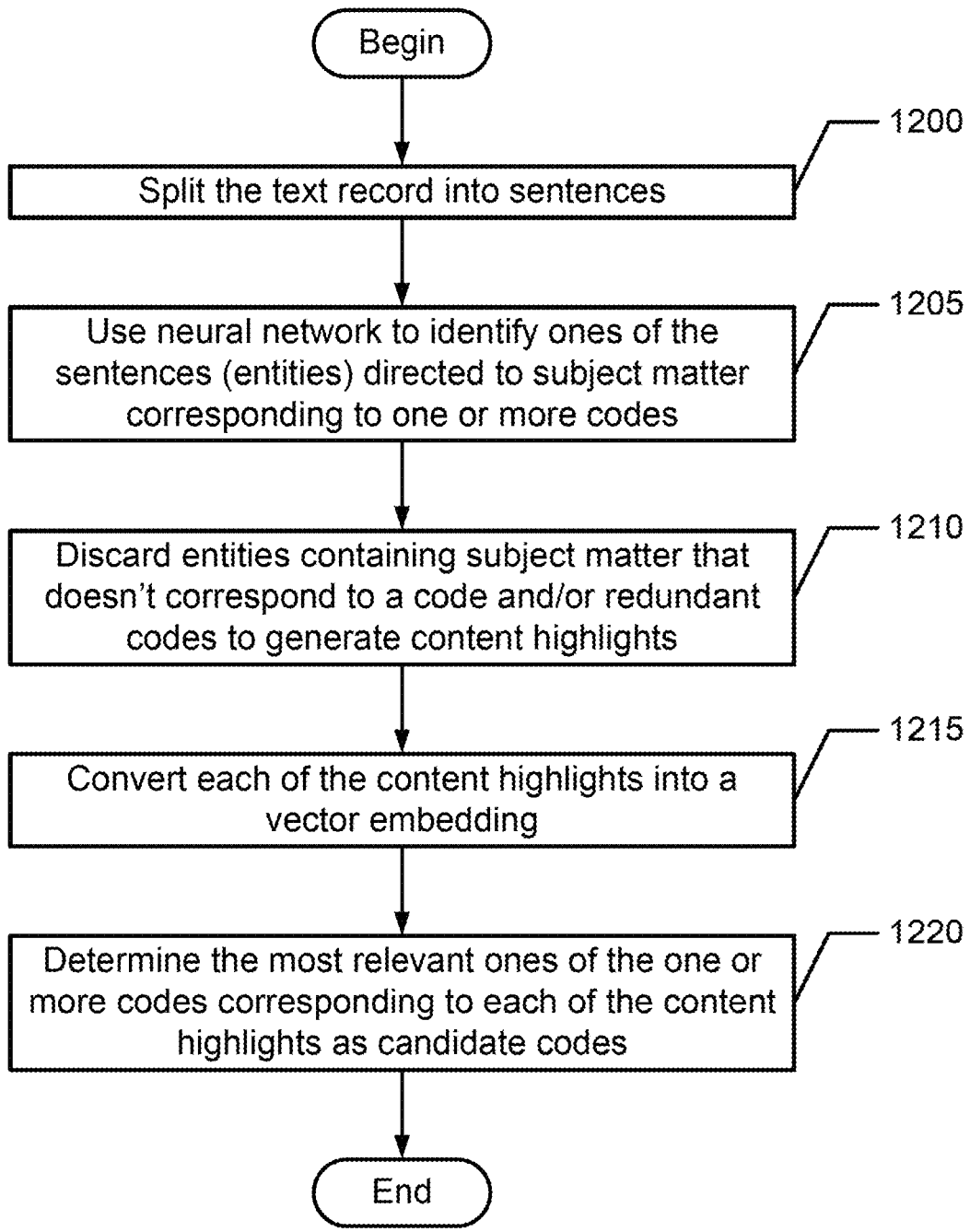

Once the record has been partitioned into sections based on encounter with those encounters that are not useful or relevant for coding disregarded, the record is passed to the entity recognition and code mapping module 225, which is configured to identify content highlights within one or more portions of the clinical information in a patient record, e.g., within each individual encounter section, and associate these content highlights with candidate codes. Referring to FIG. 12, operations begin at block 1200 where, for each encounter that has not been disregarded as irrelevant, the text record is split into sentences. A neural network may use named entity recognition at block 1205 to identify ones of the sentences that are directed to subject matter corresponding to one or more codes. These sentences that are associated with one or more codes may be termed entities. The relatively fine sentence level granularity may provide improved code coverage across the library of possible codes that may be associated with the various sentences contained in the patient's clinical record. Some embodiments of the inventive concept may provide a negation capability to disregard entities from the clinical information that are non-supportive of a code, e.g., statements that a patient doesn't have a particular disease, or are redundant, e.g., the patient has diabetes, but other text indicates that the patient has diabetes with peripheral neuropathy obviating the need to code the diabetes diagnosis. The coding may favor the more detailed diagnosis over the more general diagnosis. Thus, at block 1210, entities that contain subject matter that does not correspond to a code or are redundant are discarded to generate content highlights from the remaining non-discarded entities. Each of the content highlights may be converted into a vector embedding at block 1215. The most relevant ones of the codes that correspond to each of the content highlights are determined as candidate codes at block 1220.

Figure 13:
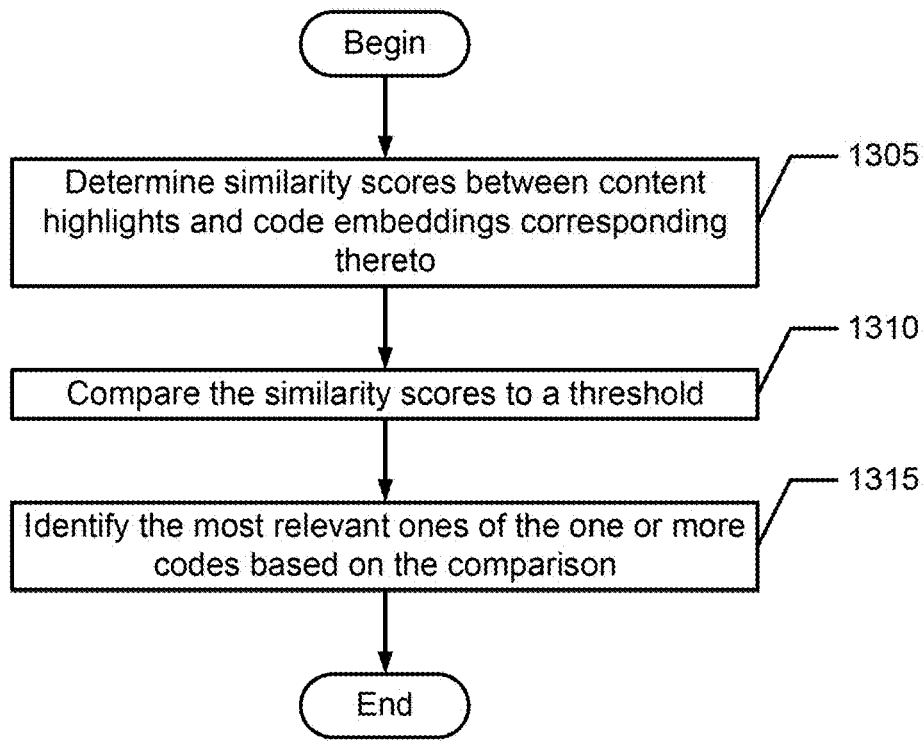

The most relevant codes for each of the content highlights may be determined in a variety of different ways in accordance with different embodiments of the inventive concept. The content highlights may be converted into numeric vector embeddings based on an average of the words in the content highlight and the codes may likewise be converted into numeric vector embeddings based on their descriptions. Referring to FIG. 13, similarity scores may be determined at block 1305 between the content highlight vector embeddings and the code vector embeddings that correspond thereto. In accordance with various embodiments of the inventive concept, the similarity scores may be determined using Euclidean distance, Manhattan distance, Chebyshev distance, and/or cosine distance. The similarity scores may be compared with a threshold at block 1310 and the k most relevant ones of the codes are identified at block 1315 based on the threshold comparison. The similarity score threshold for determining the most relevant codes for reach of the content highlights along with the number k of relevant codes may be adjusted to provide sufficient coding suggestions for the patient records without over suggesting too many codes to a user.

Figure 14:
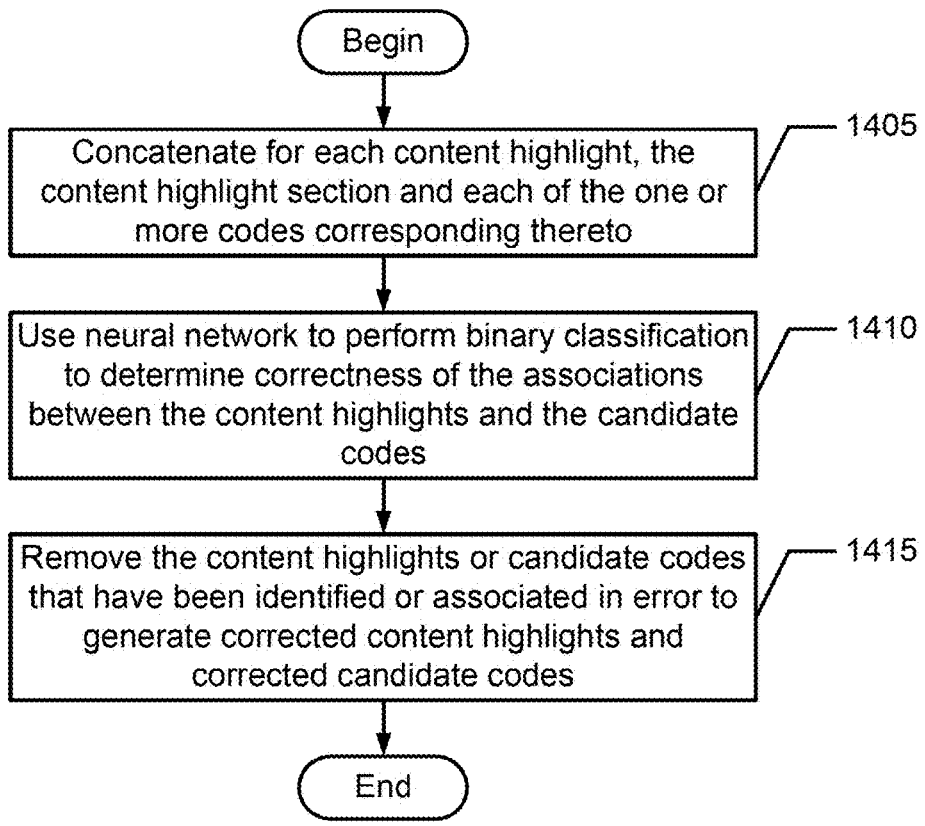

The most relevant codes for each of the highlights output from the entity recognition and code mapping module 225 are passed to the code mapping audit module 230 to evaluate the associations between the content highlights section and candidate codes. In contrast to the AI engine, e.g., neural network, used in the entity recognition and code mapping module 225, which is trained using sentences from historical patient records, the code mapping audit module 230 may be a neural network that is trained using sections, i.e., multiple sentences from historical patient records rather than single sentences. The code mapping audit module 230 may use additional context and semantic relationship information in the training process, which may be used to identify those content highlights and/or candidate codes that have been identified and/or associated with one another using the entity recognition and code mapping module 225 in error. Referring to FIG. 14, operations begin at block 1405 where the code mapping audit module 230 concatenates for each content highlight, the content highlight section and each of the candidate codes that correspond thereto. A neural network may then be used to perform a binary classification to determine the correctness of the associations between the content highlights section and the candidate codes at block 1410. Any content highlights or candidate codes that have been identified or associated in error may be removed so that the remaining content highlights and associated candidate codes may be termed corrected content highlights and associated corrected candidate codes at block 1415. The resulting corrected content highlights and associated corrected candidate codes may be used as a basis for providing code suggestions to a user for acceptance or rejection.

Figure 15:
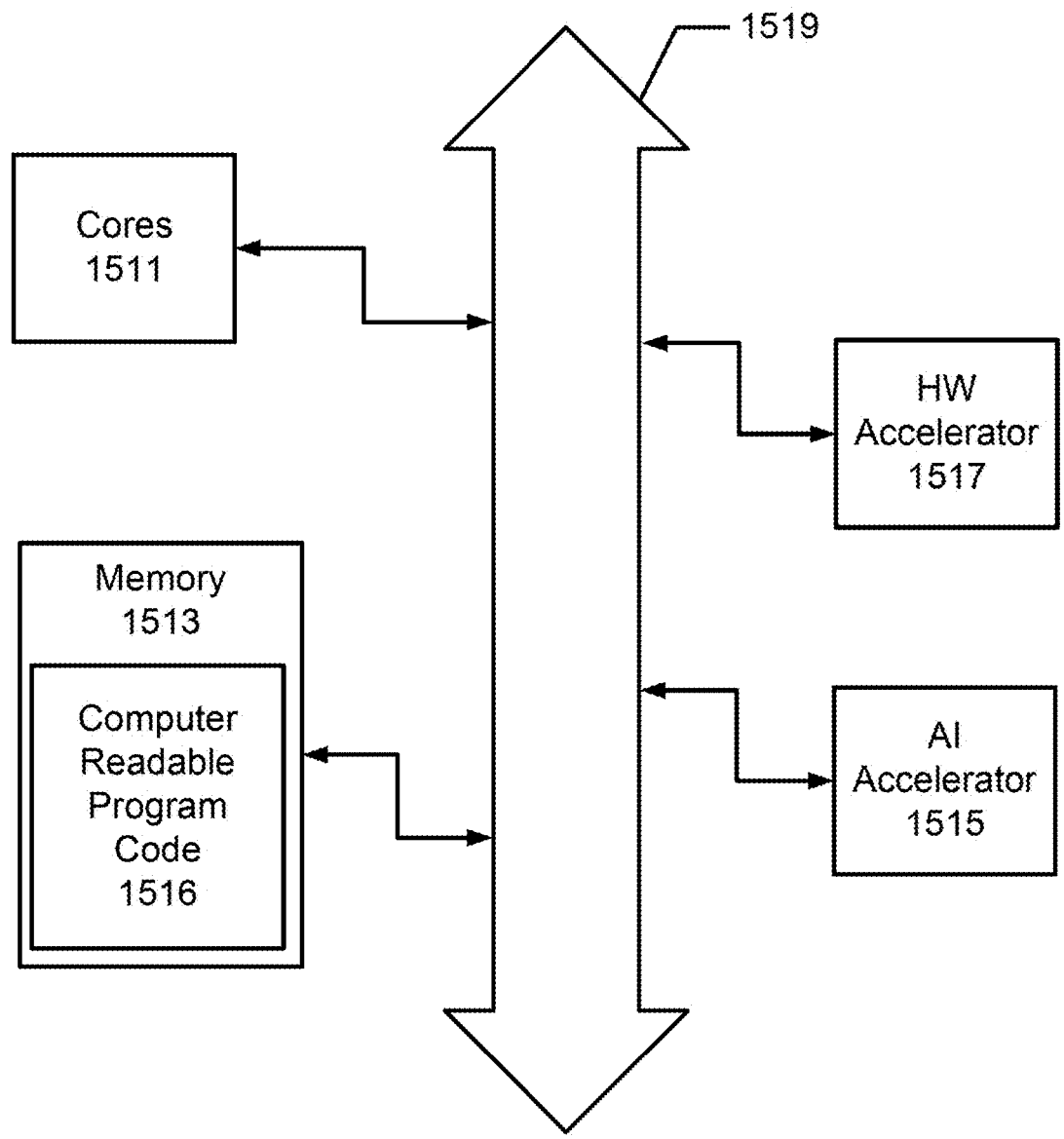
FIG. 15 is a data processing system that may be used to implement an intelligent coding DSS in accordance with some embodiments of the inventive concept.

FIG. 15 is a block diagram of a data processing system that may be used to implement the coding suggestion server 140 of FIG. 1, the PHI violation detection system 400 of FIG. 4, the encounter detection system 500 of FIG. 5, the entity recognition and code mapping system 600 of FIG. 6, and/or the code mapping and auditing system 700 of FIG. 7 in accordance with some embodiments of the inventive concept. As shown in FIG. 15, the data processing system may include at least one core 1511, a memory 1513, an artificial intelligence (AI) accelerator 1515, and a hardware (HW) accelerator 1517. The at least one core 1511, the memory 1513, the AI accelerator 1515, and the HW accelerator 1517 may communicate with each other through a bus 1519.

The at least one core 1511 may be configured to execute computer program instructions. For example, the at least one core 1511 may execute an operating system and/or applications represented by the computer readable program code 1516 stored in the memory 1513. In some embodiments, the at least one core 1511 may be configured to instruct the AI accelerator 1515 and/or the HW accelerator 1517 to perform operations by executing the instructions and obtain results of the operations from the AI accelerator 1515 and/or the HW accelerator 1517. In some embodiments, the at least one core 1511 may be an ASIP customized for specific purposes and support a dedicated instruction set.

The memory 1513 may have an arbitrary structure configured to store data. For example, the memory 1513 may include a volatile memory device, such as dynamic random-access memory (DRAM) and static RAM (SRAM), or include a non-volatile memory device, such as flash memory and resistive RAM (RRAM). The at least one core 1511, the AI accelerator 1515, and the HW accelerator 1517 may store data in the memory 1513 or read data from the memory 1513 through the bus 1519.

The AI accelerator 1515 may refer to hardware designed for AI applications.

In some embodiments, the AI accelerator 1515 may include a machine learning engine configured to facilitate operations associated with an intelligent coding DSS including the various AI engines described above with respect to the multi-stage AI engine 200 of FIG. 2. The AI accelerator 1515 may generate output data by processing input data provided from the at least one core 1515 and/or the HW accelerator 1517 and provide the output data to the at least one core 1511 and/or the HW accelerator 1517. In some embodiments, the AI accelerator 1515 may be programmable and be programmed by the at least one core 1511 and/or the HW accelerator 1517. The HW accelerator 1517 may include hardware designed to perform specific operations at high speed. The HW accelerator 1517 may be programmable and be programmed by the at least one core 1511.

Figure 16:
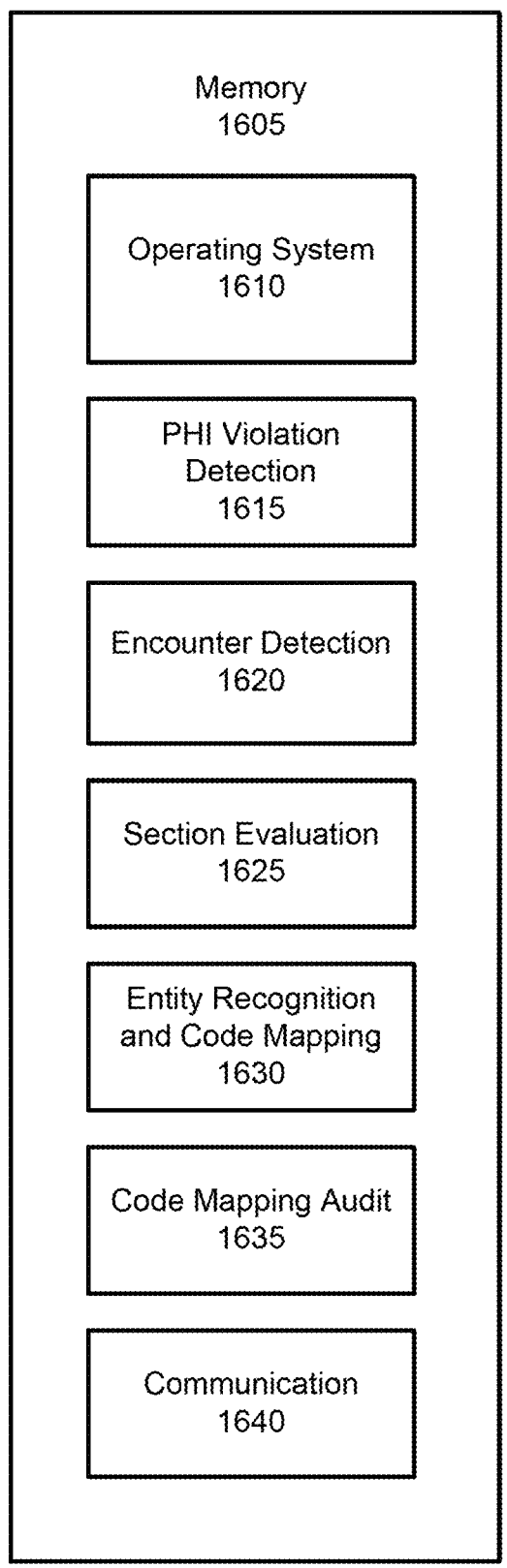
FIG. 16 is a block diagram that illustrates a software/hardware architecture for use in an intelligent coding DSS in accordance with some embodiments of the inventive concept.

FIG. 16 illustrates a memory 1605 that may be used in embodiments of data processing systems, such as the coding suggestion server 140 of FIG. 1, the PHI violation detection system 400 of FIG. 4, the encounter detection system 500 of FIG. 5, the entity recognition and code mapping system 600 of FIG. 6, the code mapping and auditing system 700 of FIG. 7, and/or the data processing system of FIG. 15, respectively, to facilitate operations of a DSS for intelligent coding of patient medical records. The memory 1605 is representative of the one or more memory devices containing the software and data used for facilitating operations of the coding suggestion server 140 and the AI/Rules engine module 145 as described herein. The memory 1605 may include, but is not limited to, the following types of devices: cache, ROM, PROM, EPROM, EEPROM, flash, SRAM, and DRAM. As shown in FIG. 16, the memory 1605 may contain seven or more categories of software and/or data: an operating system 1610, a PHI violation detection module 1615, an encounter detection module 1620, a section evaluation module 1625, an entity recognition and code mapping module 1630, a code mapping audit module 1635, and a communication module 1640. In particular, the operating system 1610 may manage the data processing system's software and/or hardware resources and may coordinate execution of programs by the processor.

The PHI violation detection module 1615 may be configured to perform one or more of the operations described above with respect to the PHI violation detection module 210 of FIG. 2, the PHI violation detection system 400 of FIG. 4, and the flowcharts of FIGS. 8-14. The encounter detection module 1615 may be configured to perform one or more of the operations described above with respect to the encounter detection module 215 of FIG. 2, the encounter detection system 500 of FIG. 5, and the flowcharts of FIGS. 8-14. The section evaluation module 1625 may be configured to perform one or more of the operations described above with respect to the section evaluation module 220 of FIG. 2 and the flowcharts of FIGS. 8-14. The entity recognition and code mapping module 1630 may be configured to perform one or more of the operations described above with respect to the entity recognition and code mapping module 225 of FIG. 2, the entity recognition and code mapping system 600 of FIG. 6, and the flowcharts of FIGS. 8-14. The code mapping audit module 1635 may be configured to perform one or more of the operations described above with respect to the code mapping audit module 230 of FIG. 2, the code mapping auditing system 700 of FIG. 7, and the flowcharts of FIGS. 8-14. The communication module 1640 may be configured to facilitate communication between the coding suggestion server 140 of FIG. 1 and/or the multi-stage AI engine of FIG. 2 and entities, such as providers, insurance claim payors, clinical record auditing entities, data entry entities, and the like that may use embodiments of the inventive concept to associate codes with patient clinical record information or extract evidence from patient clinical records to support claims, for example.

Although FIGS. 15 and 16 illustrate hardware/software architectures that may be used in data processing systems, such as the coding suggestion server 140 of FIG. 1, the PHI violation detection system 400 of FIG. 4, the encounter detection system 500 of FIG. 5, the entity recognition and code mapping system 600 of FIG. 6, the code mapping and auditing system 700 of FIG. 7, and/or the data processing system of FIG. 15, respectively, in accordance with some embodiments of the inventive concept, it will be understood that the present invention is not limited to such a configuration but is intended to encompass any configuration capable of carrying out operations described herein.

Computer program code for carrying out operations of data processing systems discussed above with respect to FIGS. 1-16 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the health care facility interface server 130 of FIG. 1, the coding suggestion server 140 of FIG. 1, the PHI violation detection system 400 of FIG. 4, the encounter detection system 500 of FIG. 5, the entity recognition and code mapping system 600 of FIG. 6, and/or the code mapping and auditing system 700 of FIG. 7, may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system." The functionality provided by the health care facility interface server 130 and the coding suggestion server 140 may be merged into a single server or maintained as separate servers in accordance with different embodiments of the inventive concept.

The data processing apparatus described herein with respect to FIGS. 1-16 may be used to facilitate operations of a DSS for intelligent coding of patient medical records according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 1605 when coupled to a processor includes computer readable program code that, when executed by the processor, causes the processor to perform operations including one or more of the operations described herein with respect to FIGS. 1-16.

Some embodiments of the inventive concept may provide a DSS that provides intelligent coding of medical record through use of a multi-stage AI engine including a plurality of pipelined AI modules. The multi-stage AI engine may automatically process clinical information contained in a patient's medical record and generate code suggestions for one or more portions of the clinical information, which can be presented to a human coder for acceptance or rejection. Much of the manual process of coding medical charts can be reduced or eliminated and the multiple tools, both internal and those supplied by the third-parties can be replaced with the intelligent coding DSS according to some embodiments of the inventive concept. For example, legacy chart filtering can be eliminated; manual chart-splitting by human agents can be replaced by an automated process provided by the multi-stage AI engine; and third-party services and tools can be replaced by the intelligent coding DSS. Replacement of the legacy components and workflows by the intelligent coding DSS, according to some embodiments of the inventive concept, may increase throughput and productivity as a patient chart does not need to be processed via multiple actors both human and via software tools. Costs can be reduced as the amount of human involvement may be reduced and external third-party fees and licenses can be avoided. Service disruption risks can be lowered by reducing or eliminating the need to rely on third-party vendors for tools. The DSS may be used by a variety of different entities including, for example, providers seeking to code medical records to facilitate generating claims therefrom to obtain payment for their services. Moreover, various features of the intelligent coding DSS may be used to correct medical records that may have PHI violations or have portions of clinical information that are incorrectly coded. Payors may use the intelligent coding DSS to audit claims by reviewing patient clinical records to obtain evidence from the clinical records to support reimbursement.

Further Definitions and Embodiments

In the above-description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random-access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

What is claimed is:

1. A computer-implemented method, comprising:
   receiving, by one or more processors, a record containing clinical information associated with a first patient;
   determining a subset of the clinical information based on discarding, by the one or more processors executing a multi-stage machine learning model that is trained using historic patient clinical information records, a feature of the clinical information;
   generating, by the one or more processors executing the multi-stage machine learning model, a code from among a set of candidate codes for one or more portions of the subset;
   wherein generating the code by the multi-stage machine learning model comprises:
      detecting, by a first machine-learned model, the subset as being associated with the first patient from among a set of data comprising data associated with a second patient and the first patient;
      detecting, by a second machine-learned model and based at least in part on the subset, a set of encounters contained in the subset;
      detecting, by a third machine-learned model based at least in part on a first encounter of the set of encounters, a first portion of the clinical information;
      generating, by a fourth machine-learned model and based at least in part on the first portion, a first embedding;
      retrieving a set of second embeddings generated by the fourth machine-learned model based on respective descriptions of the set of candidate codes;
      determining, by the fourth machine-learned model, a set of similarity scores based on a distance between respective ones of the set of second embeddings and the first embedding; and
      determining the code to associate with the first portion based on the set of similarity scores;
   causing presentation of a partition of the set of encounters, including an indication of the first portion and the code;
   receiving user input indicating approval of the code; and authorizing payment associated with the first encounter determined based at least in part on the approval and the code.

2. The computer-implemented method of claim 1, wherein the multi-stage machine learning model further comprises:
a fifth machine-learned model trained to remove at least one of a second portion of the clinical information or a second candidate code on determining, by the fifth machine-learned model, an error indication.

3. The computer-implemented method of claim 2, wherein the multi-stage machine learning model further comprises:
a sixth machine-learned model that is trained to generate a third candidate code to replace the second candidate code based on the second portion of the clinical information or a correction to the second portion of the clinical information.

4. The computer-implemented method of claim 3, further comprising:
receiving, by the one or more processors, an acceptance or a rejection of at least one of the correction to the second portion of the clinical information or the third candidate code; and
training at least one of the fourth machine learned model, the fifth machine-learned model, or the sixth-machine learned model to reduce an error determined based on at least one of the acceptance, the rejection, the second candidate code, the third candidate code, or the correction to the second portion of the clinical information.

5. The computer-implemented method of claim 2, wherein the fourth machine-learned model comprises a first neural network that is trained using the historic patient clinical information records using a first information granularity level and the fifth machine-learned model comprises a second neural network that is trained using the historic patient clinical information records using a second information granularity level that is coarser than the first information granularity level.

6. The computer-implemented method of claim 5, wherein the first information granularity level is a sentence level granularity and the second information granularity level is a section level granularity.

7. The computer-implemented method of claim 1, wherein discarding the feature of the clinical information comprises determining, by the third machine-learned model using the clinical information, an irrelevant encounter.

8. The computer-implemented method of claim 7, wherein the irrelevant encounter comprises information associated with at least one of a medication previously prescribed to the first patient, a previously diagnosed condition, a lab result, and/or a radiology result.

9. The computer-implemented method of claim 1, further comprising:
converting, by the one or more processors, the record into a text record using optical character recognition (OCR) responsive to receiving the record.

10. The method of claim 1, wherein the code comprises at least one of an International Classification of Diseases (ICD) code or a Current Procedural Terminology (CPT) code.

11. The computer-implemented method of claim 1, wherein:
the first embedding is based at least in part based on an average of words of the first portion of clinical information; and
the set of second embeddings are based at least in part on one or more sentences associated with the set of candidate codes.

12. A system, comprising:
one or more processors; and
one or more memories storing process-executable instructions that, when executed by the one or more processors, cause the one or more processors to perform operations comprising:
receiving a record containing clinical information associated with a first patient;
determining a subset of the clinical information based on discarding, by the one or more processors executing a multi-stage machine learning model that is trained using historic patient clinical information records, a feature of the clinical information;
generating, by the one or more processors executing the multi-stage machine learning model, a code from among a set of candidate codes for one or more portions of the subset;
wherein generating the code by the multi-stage machine learning model comprises:
detecting, by a first machine-learned model, the subset as being associated with the first patient from among a set of data comprising data associated with a second patient and the first patient;
detecting, by a second machine-learned model and based at least in part on the subset, a set of encounters contained in the subset;
detecting, by a third machine-learned model based at least in part on a first encounter of the set of encounters a first portion of the clinical information;
generating, by a fourth machine-learned model and based at least in part on the first portion, a first embedding;
retrieving a set of second embeddings generated by the fourth machine-learned model based on respective descriptions of the set of candidate codes;
determining, by the fourth machine-learned model, a set of similarity scores based on a distance between respective ones of the set of second embeddings and the first embedding; and
determining the code to associate with the first portion based on the set of similarity scores.

13. The system of claim 12, wherein discarding the feature of the clinical information comprises determining, by the third machine-learned model using the clinical information, an irrelevant encounter.

14. The system of claim 13, wherein the irrelevant encounter comprises information associated with at least one of medication previously prescribed to the first patient, a previously diagnosed condition, a lab result, and/or a radiology result.

15. One or more non-transitory computer readable media storing processor-executable instructions that, when executed by one or more processors, perform operations comprising:
receiving a record containing clinical information associated with a first patient;
determining a subset of the clinical information based on discarding, by the one or more processors executing a multi-stage machine learning model that is trained using historic patient clinical information records, a feature of the clinical information;

generating, by the one or more processors executing the multi-stage machine learning model, a code from among a set of candidate codes for one or more portions of the subset;

wherein generating the code by the multi-stage machine learning model comprises:

detecting, by a first machine-learned model, the subset as being associated with the first patient from among a set of data comprising data associated with a second patient and the first patient;

detecting, by a second machine-learned model and based at least in part on the subset, a set of encounters contained in the subset;

detecting, by a third machine-learned model based at least in part on a first encounter of the set of encounters a first portion of the clinical information;

generating, by a fourth machine-learned model and based at least in part on the first portion, a first embedding;

retrieving a set of second embeddings generated by the fourth machine-learned model based on respective descriptions of the set of candidate codes;

determining, by the fourth machine-learned model, a set of similarity scores based on a distance between respective ones of the set of second embeddings and the first embedding; and determining the code to associate with the first portion based on the set of similarity scores.

16. The one or more non-transitory computer readable storage media of claim 15, wherein discarding the feature of the clinical information comprises determining, by the third machine-learned model using the clinical information, an irrelevant encounter.

\* \* \* \* \*